United States Patent [19]

Arroyo

[11] Patent Number: 4,715,377
[45] Date of Patent: * Dec. 29, 1987

[54] SURGICAL INSTRUMENTATION INCLUDING A CLAMP ASSEMBLY TO FACILITATE ATTACHMENT OF BLOOD VESSEL SECTIONS

[76] Inventor: Juan Arroyo, 12200 SW. 93 St., Miami, Fla. 33186

[*] Notice: The portion of the term of this patent subsequent to Dec. 23, 2003 has been disclaimed.

[21] Appl. No.: 791,498

[22] Filed: Oct. 25, 1985

Related U.S. Application Data

[63] Continuation-in-part of Ser. No. 743,940, Jun. 12, 1985, Pat. No. 4,630,608.

[51] Int. Cl.⁴ .................. A61B 17/08; A61B 17/00
[52] U.S. Cl. .................................. 128/335; 128/346
[58] Field of Search .............. 128/335, 346, 334 R, 128/334 C, 325, 334

[56] References Cited

U.S. PATENT DOCUMENTS 4,316,470 2/1982 Braun et al. .................. 128/346

Primary Examiner—Richard C. Pinkham
Assistant Examiner—Gary Jackson
Attorney, Agent, or Firm—John Cyril Malloy

[57] ABSTRACT

Surgical instrumentation in the form of a clamp assembly specifically structured to position and maintain sections of blood vessels, such as veins and arteries, such that open ends of such blood vessel sections are maintained in immediately adjacent relation to one another and properly exposed so that such ends may be sutured or otherwise secured together. The clamp assembly is structured such that the vessel sections to be attached are supported and engaged both interiorly and exteriorly to insure maintenance of the respective open ends of such sections in a substantially outwardly flared and exposed position for attachment to one another.

13 Claims, 7 Drawing Figures

U.S. Patent  Dec. 29, 1987  Sheet 1 of 1  4,715,377
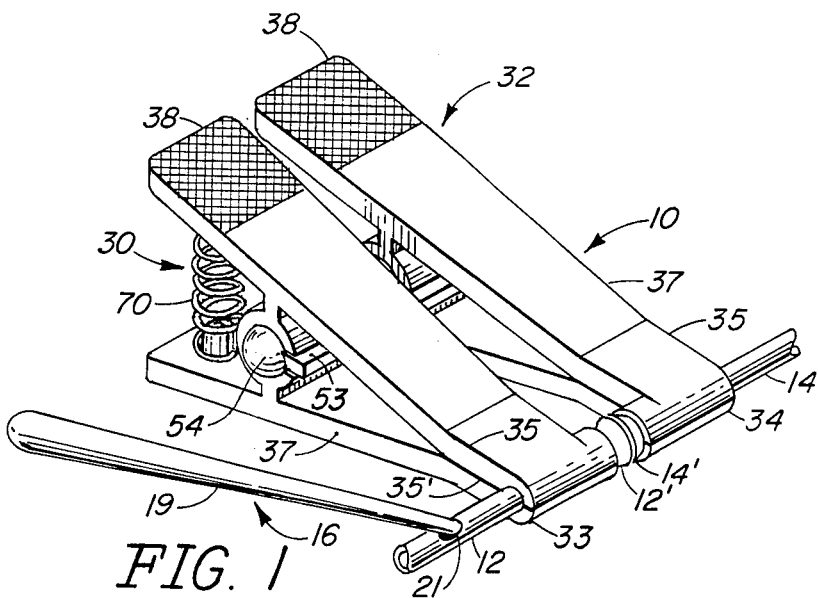
FIG. 1
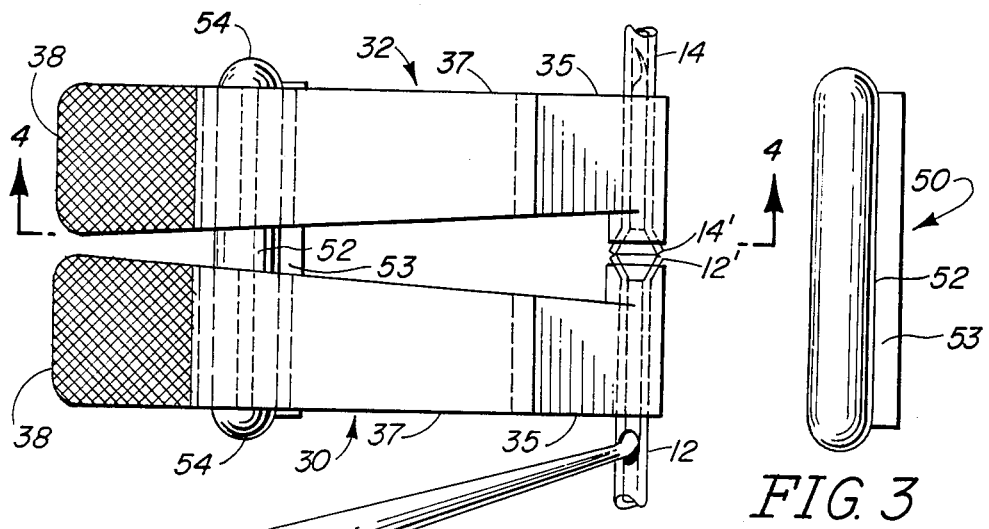
FIG. 2
FIG. 3
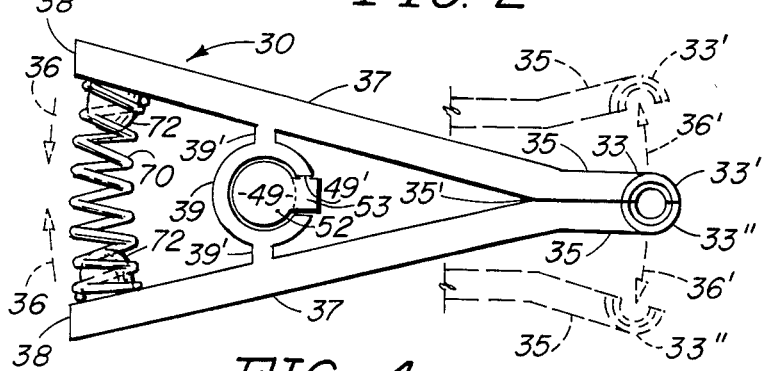
FIG. 4
FIG. 5
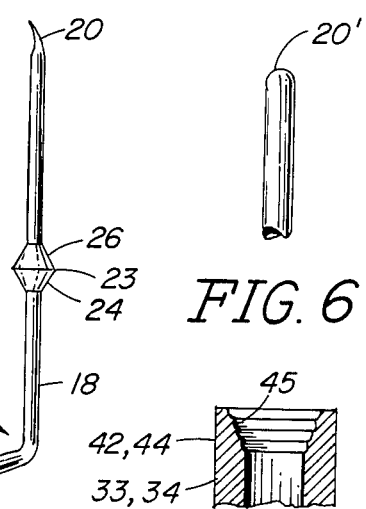
FIG. 6
FIG. 7

SURGICAL INSTRUMENTATION INCLUDING A CLAMP ASSEMBLY TO FACILITATE ATTACHMENT OF BLOOD VESSEL SECTIONS

BACKGROUND OF THE INVENTION

This is a continuation-in-part application of copending United States patent application Ser. No. 743,940 filed June 12, 1985, which has issued into U.S. Pat. No. 4,630,608.

Field of the Invention

This invention relates to a surgical instrument assembly primarily designed for the attachment of blood vessel sections in a manner which assures proper placement and maintenance of open ends of vessel sections to be attached in a properly exposed and attachable position for the application of sutures or like connecting means.

Description of the Prior Art

Vascular surgery or surgery involving blood vessels including both veins and arteries is commonly recognized in the medical profession as being difficult. Such difficulty is due in large part to the fragile nature of the structure of blood vessels and also to the extremely small size of such vessels. Accordingly, instruments including vascular clamps have to be constructed and applied with great precision in order to prevent damage or destruction to portions of the blood vessel being manipulated.

Vascular surgery dealing with the attachment or reconnection of blood vessel sections is particularly difficult and frequently time-consuming due to the extreme care which must be taken in the location, positioning and maintenance of vessel sections to be attached in proper position with one another. More specifically, open ends of separated vessel sections must be disposed in aligned and engaging relation to one another and further, such open ends must be maintained in an attachable position or engagement with one another and properly exposed so that the surgeon can suture such open ends together or apply other connecting means. In order to accomplish such positioning and maintenance of the open ends in properly exposed position, many instruments currently in use in the performing of such surgical techniques are less than totally satisfactory.

Accordingly, there is a recognized need in the medical profession for proper surgical instrumentation particularly designed and constructed for the positioning and maintenance of blood vessel sections and open ends thereof in an attachable position which is readily exposed for the application of sutures and like connecting means to the open ends.

SUMMARY OF THE INVENTION

The present invention is directed towards surgical instruments preferably in the form of a clamp assembly which is specifically designed to embrace, position, and maintain blood vessel sections, to be attached to one another, in engaging relation and properly exposed for the application of sutures or like connecting means serving to attach such vessel sections to one another.

More specifically, the subject surgical instrumentation comprises a support means having an elongated supporting pin or like structure with either a blunted or sharpened free end. Such pin and more specifically the elongated portion thereof is disposed on the interior of both vessel sections to be attached. A support platform is formed along the length of the elongated portion and is dimensioned and configured to extend transversely outward from the pin. The pin and the platform are positioned such that the open ends of the vessel sections to be attached engage opposite sides of the platform and are forced to flare outwardly when so positioned.

The positioning of the open ends of the vessel sections in the manner described is established and maintained through the provision of two sleeve elements. Each sleeve element is disposed in surrounding relation to one vessel section immediately adjacent the open end thereof. Each sleeve element is structured to define a free end of a clamp. Preferably, each of the clamps has outwardly extending lever arms structured and disposed to pivot about a fulcrum structure wherein one end of each lever arm is integrally secured to a bifurcated or separable portion of the sleeve element associated with that clamp. Pivotal movement of the lever arms causes the separable sections of the sleeve element to move into and out of surrounding engagement relative to a vessel section.

Further, each sleeve element includes a proximal end having an outwardly flared or somewhat funnel-like configuration. This outwardly flared configuration of each proximal end of each sleeve element substantially corresponds to a correspondingly positioned side of the support platform located on the interior of the vessels and positioned to engage the interior surface of open ends thereof. Correspondingly, the interior surface of the proximal flared end of each sleeve element is textured, roughened or specifically structured to somewhat frictionally engage the exterior surface of the vessel section immediately adjacent the open end causing it to be forced and maintained on the corresponding side of the support platform of the support pin and maintained in such outwardly flared position. Maintenance of the respective open ends of the respective vessels in such position serves to position both open ends in exposed and substantially engaging orientation so as to define an attachable position of the open ends.

Further, an important feature of the present invention is the maintaining of the respective open ends in such outwardly flared position, while being connected, so as to prevent the formation of any restriction or narrowing of the vessel at the junction of the open ends. Such narrowing or restricted configuration would cause turbulence during blood flow and possible clotting or occlusion of the vessel at this area due to such turbulence.

When each clamp is properly positioned relative to the respective vessel sections so as to maintain the open ends thereof in the aforementioned attachable position, a securement means in the form of a securement pin is connected between the clamps so as to maintain such clamps in spaced apart but relatively fixed position relative to one another. The engaged vessel section may therefore be manipulated and generally oriented into the proper position for accomplishing securement of the open ends together. However, the placement of such securement pin serves to maintain the respective clamps in secured position about the respective vessel sections.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is an isometric view of the clamp assembly disposed in engaging relation to vessel sections being attached such that respective open ends thereof are maintained in an attachable position.

FIG. 2 is a top plan view of the embodiment of FIG. 1.

FIG. 3 is a front elevational view showing details of a securement pin also represented in FIGS. 1 and 2.

FIG. 4 is a side view of a single clamp of the clamp assembly.

FIG. 5 is a top plan view of a supporting pin mounted on the interior of the blood vessel sections to be attached.

FIG. 6 is a plan view in partial cutaway showing another embodiment of the supporting pin of FIG. 5.

FIG. 7 is a detail sectional view in partial cutaway showing the structural configuration of the proximal end of each sleeve element of each clamp.

Like reference numerals refer to like parts throughout the several views of the drawings.

DETAILED DESCRIPTION OF THE PREFERRED EMBODIMENT

As clearly shown in FIG. 1, the surgical instrumentation of the present invention is generally indicated as 10 and comprises a clamp assembly designed to engage and maintain in an attachable position, blood vessel sections 12 and 14 such that their corresponding open ends 12' and 14' are maintained in an attachable position and exposed so that the surgeon has clear access to apply sutures or any applicable connecting means.

More specifically, the assembly 10 comprises a support means generally indicated as 16 having an elongated supporting pin portion 18 and an outwardly extending handle 19 preferably angularly oriented relative to the length of the elongated supporting pin 18. With reference to FIG. 5, the free end of the elongated portion 18 as at 20 is sharpened or pointed so that it may enter a lateral zone as at 21 of one of the vessels 12 and be oriented in coaxial relation to such vessel. The elongated pin portion 18 is of such a length as to pass into a similar coaxial position relative to vessel section 14 so as to assume an interior supporting position as represented in broken lines in FIG. 2. The support means 16 further includes a support platform 23 having oppositely disposed and substantially angularly oriented sides 24 and 26. The platform as well as the sides 24 and 26 are dimensioned and structured to extend transversely outward from the elongated portion 18 and longitudinal axis thereof. Such angular orientation of the sides 24 and 26, when mounted on the interior of the vessel sections 12 and 14 position the overlying open ends 12' and 14' in a substantially outwardly flared position as shown in FIGS. 1 and 2. As also represented therein, positioning and maintenance of the open ends 12' and 14' in this outwardly flared position and substantially adjoining relation to one another define an exposed, attachable position of the respective open ends wherein clear access is provided for the surgeon to secure such open ends together through proper connecting means as set forth above. Another embodiment of the elongated portion 18 of support means 16 as shown in FIG. 6 includes a rounded or non-sharpened point 20'. When utilizing this embodiment, a small incision is made in the vessel being repaired or connected and the rounded point 20' passes therethrough into the position shown in FIG. 2.

In order to position and maintain the vessel sections 12 and 14 in the positions represented in FIGS. 1 and 2, a clamp assembly comprising one clamp for each vessel section and generally represented as 30 and 32. As shown in FIGS. 1, 2 and 4, each clamp is substantially identically structured and includes a sleeve element 33 and 34 disposed in at least partially surrounding and engaging relation to a respective vessel section 12 and 14. The sleeve element of each clamp 30 and 32 defines an end portion thereof and is specifically designed to include a bifurcated construction comprising separable portions 33' and 33" as shown in FIG. 4. For purposes of clarity, detailed structural features of each of the clamps will be made with reference to specific clamp 30 as represented in FIG. 4. However, each of the sleeve elements 33 and 34 include such a bifurcated constuction and separable sleeve portions.

Each clamp 30 and 32 further includes two outwardly extending lever arms comprising a first portion 35 and a second portion 37 integrally secured together in a one piece construction. A fulcrum structure 39 is disposed in substantially sandwiched relation between the interior surfaces of the second portions 37 of each lever arm such that depression of the free ends 38 thereof as indicated by directional arrows 36 causes a pivotal movement of the second portions 37 about fulcrum structure 39 and a separation of the separable portions 33' and 33" of the sleeve element 33. Further structural features of the fulcrum structure 39 includes a central aperture 49 which is partially open as at 49' to facilitate opening and closing and/or relative pivotal movement of the lever arm portions 37 of each clamp relative to one another. The central aperture 49 is dimensioned and configured to allow passage therethrough of connecting pin 52 so as to effectively connect and maintain the two clamp assemblies in fixed, spaced apart relation to one another when vein sections or segments 12' and 14' are secured in the position shown in FIGS. 1 and 2. Also, the fulcrum structure 39 is integrally connected between the lever arm portions 37 of each lever arm by means of outwardly extending flanges 39' defining an integral connection between the interior surface of each of the lever arm portions 37 and the fulcrum 39. Accordingly, it is readily seen that each of the clamps 30 and 32 is formed from an integral, one piece construction and made from a plastic material or the like which is inherently flexible so as to allow relative movement of the clamp arms 37 to one another about fulcrum structure 39 due to the presence of the integrally formed and interconnecting flanges 39'. As also clearly shown in FIG. 4, a biasing spring 70 is disposed between the lever arm adjacent the free ends thereof and maintained in place by integrally formed outwardly extending protrusions 72.

Another structural feature of the present invention is best shown in FIGS. 1 and 4 and comprises the configuration of first portion 35 of each arm having its undersurface as at 35' cooperatively arranged for substantially coplanar engagement with one another in order to stabilize and support mating engagement between the separable portions 33' and 33" of the sleeve element 33. As clearly shown in FIG. 4, the integral construction and structural configuration of the end portions 35 of each lever arm is cooperative with the remainder of the lever arm as at 37 so as to cause mating engagement in the aforementioned coplanar relation of the inner surfaces 35' based on pivital movement of the free ends 38 which may be roughened, for better gripping, as shown in FIGS. 1 and 2.

From the structure as set forth above, it is readily seen that depression of free ends of the second section 37 of each lever arm causes pivotal movement of these ends in the direction indicated by directional arrows 36. Concurrently, separable sections 33' and 33" are separated in accordance with directional arrows 36' and the respective sleeve elements 33 and 34 may be secured in surrounding relation to the respective vessel sections 12 and 14 or removed therefrom.

Another feature of the present invention is the construction of each proximal end 42 and 44 to have a substantially outwardly flared or at east partially funnel-like configuration as clearly shown in FIG. 7. Further, the inner surface 45 of each proximal end 42, 44, is textured or otherwise configured to facilitate the engagement and maintenance of a correspondingly positioned opened end 12' and 14' of the respctive vessel sections 12 and 14. Such "textured" structure of the inner surface as at 45 may be any of a number of specific structural configurations such as roughened, knurled, or ridged. the textured inner surface 45 should be capable of creating at least a minimal frictional equipment with the exterior surface of the vessel sections 12 and/or 14 without causing damage thereto. A firm gripping engagement is thereby maintained to accomplish accurate positioning of the respective open ends 12' and 14' onto the respective sides 24 and 26 of the support platform 23 of support pin 18. It should be noted however that the structural configuration of inner surface 45 should not be such as to cause damage to the exterior surface or overall structure of the open ends 12' and 14'. It should be further noted that the sides 24 and 26 are correspondingly configured and the angled surfaces thereof substantially correspond to and are in alignment with the flared inner surface 45 such that the open ends 12' and 14' may be positioned and maintained in the shown outwardly flared position and in adjoined and accessible relation to one another so as to allow the surgeon to apply applicable connecting means to secure such open ends to one another. As set forth above, such outwardly flared positioning at the junction of the open ends, after connection, is important for the purposes of eliminating any restriction at this junction and the attendant clotting and/or occlusion.

Once the respective clamps 30 and 32 are positioned in engaging and maintaining relation to the vessel sections 12 and 14, it is important that such clamps be maintained in their relative positions. Accordingly, a securement means generally indicated as 50 is provided in the form of a connecting pin 52 having end portions 54. As shown in FIGS. 1 and 2, the securement means or connector pin 52 is structured and dimensioned to fit on the interior 49 of the fulcrum structure 39. The fulcrum structure 39 being formed into an at least partially cylindrical configuration and being open as at 49' to the interior 49 thereof. (See FIG. 4). The end portions 54 may project outwardly from the respective fulcrum structures 39 as associated with the clamps 30 and 32. The pin 52 extends between the clamps 30 and 32 and the free ends 54 may extend outwardly therefrom. The diameter of pin 52 is dimensioned to snugly fit within channel 49 of fulcrum structure 39 but be removable therefrom. The pin 52 further includes an elongated laterally extending flange 53 projecting through the opening 49' of end clamp. The disposition of the flange 53 relative to both clamps 30 and 32 prevent relative rotation of either clamp about pin 52. The clamps are thereby maintained in an adjacent, aligned relation to one another. Fulcrum structure 39 allows pivotal movement of arms 37 of each clamp relative to one another against biasing spring 70. Opening 49' spread apart somewhat when such pivoting occurs in the direction of arrows 36. Such movement occurs while pin 52 is maintained in place as shown in FIGS. 1 and 2.

What is claimed is:

1. A surgical instrumentation assembly of the type primarily designed for the positioning of open ends of blood vessel sections in aligned relation to one another for attachment thereof, said assembly comprising:
   (a) support means for aligned positioning of the vessel sections relative to one another and structured for interior, supporting engagement of both vessel sections,
   (b) said support means including an elongated portion disposable in coaxial relation concurrently within both vessel sections,
   (c) positioning means structured for exterior engagement with said vessel sections and aligned positioning and maintenance of the open ends into attachable position relative to one another,
   (d) said positioning means comprising a clamp assembly including two clamps disposable in interconnected, adjacently spaced relation to one another and each clamp comprising a sleeve element configured and dimensioned for surrounding and engaging relation to respective vessel sections,
   (e) said clamp further comprising two elongated lever arms each connected at one end thereof to said sleeve element and extending outwardly therefrom to respective free ends disposed in spaced relation to one another,
   (f) a fulcrum structure disposed between said lever arms of each clamp and pivotally interconnected to said lever arms and structured to allow pivotal movement of said lever arms relative to one another,
   (g) said lever arms, fulcrum structure and sleeve element of each clamp being of an integral, one piece construction,
   (h) securement means for positioning said sleeve elements relative to one another and structured for interconnecting said sleeve elements to one another for maintenance thereof into engageable relation to said respective vessel sections, and
   (i) said support means and said sleeve elements relatively structured and dimensioned to maintain the respective vessel sections in sandwiched relation therebetween and the open ends of the vessel sections in adjacent, aligned relation to one another.

2. An assembly as in claim 1 wherein said securement means is structured for removable interconnection of said sleeve elements and structured for maintenance of said sleeve elements in fixed, spaced relation to one another and in engagement with respective vessel sections.

3. An assembly as in claim 1 wherein said support means further comprises a platform formed on said elongated portion and configured to extend substantially transversely outward therefrom, said platform disposed to engage the open ends of the respective vessel sections and maintain the open ends in a substantially outwardly flared orientation for connection to one another.

4. An assembly as in claim 3 wherein each proximal end of said sleeve elements comprises an outwardly flared configuration disposed in facing relation to one another and in at least partially surrounding engagement with the exterior surface of the respective open ends thereof, said platform and said respective flared proximal ends cooperatively configured and dimensioned for maintenance of the open ends in an outwardly flared orientation for connection to one another.

5. An assembly as in claim 4 wherein each of said proximal ends includes a textured inner surface disposable in engaging relation to the exterior surface of each vessel section.

6. An assembly as in claim 1 wherein each sleeve element of each clamp comprises a bifurcated construction, each of said lever arms secured at one end to a separable portion of said sleeve element, said separable portions positionable into and out of separating relation to one another and surrounding relation to a vessel section upon pivotal movement of said level arms relative to said fulcrum structure.

7. An assembly as in claim 1 wherein said securement means comprises a connecting pin secured to each of said clamps and structured to maintain said clamps in fixed, spaced relation to one another and said sleeve elements in surrounding relation to respective vessel sections.

8. An assembly as in claim 7 wherein said connecting pin is removably interconnected to each clamp and attachable thereto adjacent said respective fulcrum structures.

9. An assembly as in claim 1 wherein said fulcrum structure of each clamp comprises a channel including an at least partially cylindrical configuration and a central opening therethrough extending substantially transverse to the length of said respective clamp, said channel and said central opening dimensioned and configured to removably receive said securement means therein.

10. An assembly as in claim 9 wherein said fulcrum structure comprises a peripheral opening communicating with said central opening and facilitating pivotal interconnection of said lever arms and relative movement of said lever arms.

11. An assembly as in claim 1 wherein one end of each lever arm of each clamp adjacent said respective sleeve element is disposed and configured for substantially planar registry of inner surface portions thereof.

12. A surgical instrumentation assembly of the type primarily designed for the positioning of open ends of blood vessel sections in aligned relation to one another for attachment thereof, said assembly comprising:

(a) support means for aligned positioning of the vessel sections relative to one another and structured for interior, supporting engagement of both vessel sections, (b) said support means including an elongated portion disposable in coaxial relation concurrently within both vessel sections.

(c) positioning means structured for exterior engagement with said vessel sections and aligned positioning and maintenance of the open ends into attachable position relative to one another, (d) said positioning means comprising a clamp assembly including two clamps disposable in interconnected, adjacently spaced relation to one another and each clamp comprising a sleeve element configured and dimensioned for surrounding and engaging relation to respective vessel sections, (e) each of said clamps further comprising two elongated lever arms each connected at one end thereof to said sleeve element and extending outwardly therefrom to respective free ends disposed in spaced relation to one another, (f) a fulcrum structure disposed between said lever arms of each clamp and pivotally interconnected to said lever arms and structured to allow pivotal movement of said lever arms relative to one another, (g) said lever arms, fulcrum structure and sleeve element of each clamp being of an integral, one piece construction, (h) securement means for interconnecting said sleeve elements relative to one another and maintaining said sleeve elements into engageable relation with said respective vessel sections, (i) said support means and said sleeve elements relatively structured and dimensioned to maintain the respective vessel sections in sandwiched relation therebetween and the open ends of the vessel sections in adjacent, aligned relation to one another, said fulcrum structure of each clamp comprising a channel including an at least partially cylindrical configuration and a central opening therethrough extending substantially transverse to the length of said respective clamp, said channel and said central opening dimensioned and configured to removably receive said securement means therein, (j) a peripheral opening formed in each of said channels and communicating with said central opening thereof and facilitating pivotal interconnection of respective ones of said lever arms in relative movement therebetween, and (k) said fulcrum structure further comprising a plurality of flange elements integrally interconnected between said cylindrical configuration and said fulcrum structure and an interior surface of each of said lever arms.

13. An assembly as in claim 12 wherein said securement means comprises a connecting pin removably connected to each clamp by passing through said respective channel thereof, said connecting pin including an elongated flange extending substantially along the length thereof and laterally outward therefrom, said elongated flange disposed to project outwardly concurrently through each peripheral opening of each clamp, whereby said clamps are prevented from rotating relative to one another about said connecting pin.

* * * * *